(12) United States Patent
Srivastava et al.

(10) Patent No.: US 8,518,992 B2
(45) Date of Patent: Aug. 27, 2013

(54) METHOD OF SYNTHESIS AND PURIFICATION OF N-6-TRIMETHYL-L-LYSINE AND DERIVATIVE COMPOUNDS

(76) Inventors: Suresh C. Srivastava, Burlington, MA (US); Sant K. Srivastav, Burlington, MA (US); Stanley J. Szymanski, Jr., Sewickley, PA (US)

(*) Notice: Subject to any disclaimer, the term of this patent is extended or adjusted under 35 U.S.C. 154(b) by 0 days.

(21) Appl. No.: 12/932,937

(22) Filed: Mar. 9, 2011

(65) Prior Publication Data

US 2011/0166379 A1     Jul. 7, 2011

Related U.S. Application Data

(62) Division of application No. 11/105,165, filed on Apr. 13, 2005, now Pat. No. 7,932,287.

(60) Provisional application No. 60/601,095, filed on Aug. 12, 2004.

(51) Int. Cl.
*A61K 31/195* (2006.01)

(52) U.S. Cl.
USPC .................................................. 514/561

(58) Field of Classification Search
None
See application file for complete search history.

(56) References Cited

PUBLICATIONS

Vaz et al (Clin Chem 48(6):826-834, 2002).*
Biologics Consulting Group (Guide to Inspections of Lyophilizaation of Parenterals, 1993).*

* cited by examiner

*Primary Examiner* — Craig Ricci
(74) *Attorney, Agent, or Firm* — Law Offices of Indu M. Anand; Indu M. Anand, Esq.

(57) ABSTRACT

The invention provides a method of synthesis of N-6-trimethyl-L-lysine (TML) derivative compounds for potential treatment of disorders resulting from deficiencies in the TML-carnitine pathway. The invention also provides a method of purification of TML and TML derivative compounds. The treatment of conditions of the diseases late infantile neuronal ceroid lipofuscinosis (LINCL) and neuronal ceroid lipofuscinosis (NCL) with TML were shown in the original parent application.

2 Claims, No Drawings

METHOD OF SYNTHESIS AND PURIFICATION OF N-6-TRIMETHYL-L-LYSINE AND DERIVATIVE COMPOUNDS

CROSS-REFERENCE TO RELATED APPLICATIONS

This is a division of application Ser. No. 11/105,165, filed Apr. 13, 2005, now U.S. Pat. No. 7,932,287 which claims priority from provisional application No. 60/601,095 filed on Aug. 12, 2004, and it incorporates the subject matter identified as Invention III and IV in the Requirement for Restriction/Election of Apr. 13, 2007, in the parent application. All materials referenced in the prior provisional and non-provisional applications are hereby incorporated by reference. This includes, but is not limited to, all specifications, drawings, and like materials.

Related divisional applications by the same inventors claiming similar priority include "Derivative Compounds of N-6-Trimethyl-L-Lysine for Therapeutic Use," application Ser. No. 12/932,940; "Method of Treating Human Being for a Class of Metabolic Defects and Energy Production Disorders," application Ser. No. 12/932,939; and "Method of Treating a Human Being for a Class of Neurological Defects and Seizure Disorders," application Ser. No. 12/932,938.

All books, manuals, articles, and papers that are cited herein are hereby incorporated by reference in their entirety.

BACKGROUND OF THE INVENTION

1. Field of Invention

This invention relates to the synthesis of derivative compounds of N-6-trimethyl-L-lysine.

2. Description of Related Art

All material referenced in the prior provisional and non-provisional applications are hereby incorporated by reference.

In the parent application Ser. No. 11/105,165, allowed on Nov. 17, 2010 to issue as a patent, it was shown by carefully compiled experimental results and other scientific demonstration, that therapeutic use of TML may successfully arrest, and in certain respects, reverse the degeneration associated with the group of progressive neurological diseases called neuronal ceroid lipofuscinoses (NCL).

The parent application described the symptoms and common as well as distinct characteristics of the spectrum of NCL group, including the following: Batten Disease, Santavuori disease, Late-Infantile Neuronal Ceroid Lipofuscinoses (LINCL), Speilmeyer-Sjogren disease, Kuf disease, Parry disease, Bernheimer-Seitelberger syndrome, Bielschowsky amaurotic idiocy, Bielschowsky disease, Jansky-Bielschowsky disease, Seitelberger disease, late infantile amaurotic idiocy, late infantile Batten disease, subacute late infantile neuronal ceroid-lipofuscinosis, Zeman-Dyken-Lake-Santavuori-Savukoski disease.

At the genetic level, the neuronal ceroid lipofuscinoses (NCL's) result from mutations in at least eight genes, and these mutations are responsible for causing the various expressions of the neurodegenerative diseases collectively identified as NCLs. A summary background of these mutations and a survey of the background reference literature were given in the parent application. See Table A by Gene Locus.

TABLE A

Neuronal Ceroid Lipofuscinosis - Summary of Symptoms

| SYMPTOMS | CLN1 | CLN2 | CLN3 | CLN4 | CLN5 | CLN6 | CLN7 | CLN8 | CLN9 | CLN10 |
|---|---|---|---|---|---|---|---|---|---|---|
| Dementia | Yes | Yes | Yes | Yes | Yes | Yes | | | | |
| Seizures | Yes | Yes | Yes | Yes | Yes | Yes | Yes | Yes | Yes | yes (hyperknetic movements, hand/feet tremors) |
| Progressive Visual Failure | Yes | Yes | Yes | Yes | Yes | Yes | Yes | No | Yes | newborn infant |
| Mental Retardation | Yes | Yes | Yes | Yes | Yes | | Yes | Yes | | Yes |
| Loss Of Speech | Yes | Yes | Yes | | Yes | | Yes | | Yes | yes |
| Regression of Motor Development | Yes | Yes | | | Yes | | Yes | | Yes | yes |
| Ataxia | Yes | Yes | | Yes | Yes | | Yes | | Yes | yes |
| Muscular Hypotonia/Dystonia | Yes | Yes | | Yes | Yes | | | | | yes |
| Microcephaly | Yes | | | | | | | | | |
| Optic Atrophy/Macular Degeneration Retinitis Pigmentosa | Yes | Yes | Yes | | Yes | | | | | |
| Myoclonus | Yes | Yes | Yes | Yes | Yes | | Yes | No | | |
| Cerebellar Atrophy | Yes | Yes | Yes | Yes | | | | | | yes |
| Quadraparesis | | Yes | | | | | | | | |

TABLE A-continued

Neuronal Ceroid Lipofuscinosis - Summary of Symptoms

| SYMPTOMS | CLN1 | CLN2 | CLN3 | CLN4 | CLN5 | CLN6 | CLN7 | CLN8 | CLN9 | CLN10 |
|---|---|---|---|---|---|---|---|---|---|---|
| Refractory Epilepsy | | Yes | | | | | | | | |
| Behavioral Involvement (Anger Outburst, Physical Violence) | | Yes | Yes | | | | | | | |

Table A Notes:
1. According to Mole et al.,2005, the clinical course of the NCL's include progressive dementia, seizures, and progressive visual failure (Full text available at http://www.springerlink.com/content/xu2406100j81034w/fulltext.pdf ).
2. A 'Yes' means that the symptom is a characteristic of the disease. A 'No' means that the OMIM synopsis from clearly stated that the specific symptom is NOT characteristic of that particular NCL. An empty space for a particular symptom does not necessarily preclude it from being part of the characteristics of that particular NCL; it was not mentioned specifically in the OMIM synopsis. For instance, CLN6 is an LINCL (CLN2) variant. It did not specifically mention Mental Retardation or Loss of Speech or Cerebellar Atrophy; but it would be reasonable that Mental Retardation/Loss of Speech/Cerebellar would be part of the continuum.
CLN1 (Infantile)
CLN2 (Late Infantile)
CLN3 (Juvenile)
CLN4a (Kufs Disease)
CLN5 (Late Infantile, Finnish Variant)
CLN6 (Late Infantile, Variant, Included, Variable age at onset)
CLN7
CLN8
CLN8 (Northern Epilepsy Variant)
CLN9
CLN10 Cathepsin D-Deficient, Congenital No generally effective treatment for many of the diseases mentioned above is currently available and these diseases are generally fatal. The line of treatment proposed in the parent application is based on administering, in the form of a therapeutic agent of very high purity, any of the following to a human being in need thereof: (a) N-6-trimethyl-L-lysine, (b) a prodrug thereof, or (c) a pharmaceutically acceptable salt of N-6-trimethyl-L-lysine or said prodrug.

The one common characteristic in all these disorders has been found to be the accumulation of autofluorescent storage material in all tissues, particularly pronounced in the central nervous system. This characteristic has been tied to the fundamental role of L-carnitine in metabolism, such as the prevention of hyperammonimia, lipid peroxidation and fatty acid metabolism. It has also been found that availability of TML, as the rate limiting step in the regulation of feedback inhibition for L-carnitine biosynthesis, is crucial to the biosynthesis of L-carnitine. (Schematic 1, by F. M. Vaz and R. J. A. Wandars, Biochem. J., 361, 417-429, 2002).

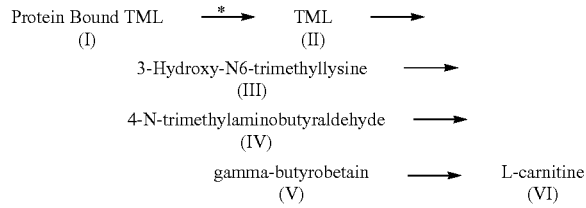

Schematic 1-Biosynthesis of L-Carnitine from TML (feedback regulation of TML)

*(rate limiting step for L-carnitine biosynthesis and feedback inhibition of L-carnitine)

A summary of the role of carnitine, which was described in greater detail in the parent application, is outlined below:

(a) From a biochemical standpoint, L-carnitine plays an essential role in energy metabolism. In fatty acid metabolism, it serves as shuttle between the mitochondrial membrane and the mitochondria inner-workings permitting breakdown of the long carbon fragment. A major part of that role is in maintaining a balance between the concentration of a compound called acyl CoA in the cell compartments and in sugar metabolism.

(b) Optimal ATP production in humans from either dietary or stored fatty acids is dependent on L-carnitine. L-Carnitine has several roles, most of which involve conjugation of acyl residues to the b-hydroxyl group of the L-carnitine with subsequent translocation of this complex from one cellular compartment to another.

(c) Defects in fatty acid oxidation are a source of major morbidity and are potentially rapidly fatal. Fatty acid oxidation defects encompass a spectrum of clinical disorders, including recurrent hypoglycemic, hypoketotic encephalopathy or Reye-like syndrome in infancy with secondary seizures and potential developmental delay, progressive lipid storage myopathy, recurrent myoglobinuria, neuropathy, and progressive cardiomyopathy.

(d) Administration of L-carnitine prevents acute ammonia toxicity and enhances the efficacy of ammonia elimination as urea and glutamine. In addition the cytotoxic effects of ammonia, possibly arising from lipid peroxidation, are ameliorated by L-carnitine. These data indicate the feasibility of utilization of L-carnitine in the therapy of human hyperammonemic syndromes.

(e) L-Carnitine deficiency can be defined as a decrease of intracellular L-carnitine, and is a factor, inter alia, in the inhibition of the mitochondrial oxidation of long-chain fatty acids during fasting, heart or liver failure (which may in turn cause encephalopathy by hypoketonemia, hypoglycemia and hyper-ammonium), and lower acetylcholine synthesis in the nervous system.

L-carnitine plays a key, and critical, role in enhancing fat metabolism. It appears evident that L-carnitine works by transporting fatty acids to be burned for fuel, increasing both energy supply and lean muscle mass. Most reports found that unless an individual is deficient in L-carnitine, it is an unnecessary ergogenic aid. This contrasts with an apparent need in case of L-carnitine deficiency (e.g., in the case pursued by the inventors of Late Infantile Neuronal Ceroid Lipofuscinosis—one form of Batten Disease), of the correct operation of the endogenous production of L-carnitine. This need was corroborated in the observations of dogs with Batten Disease given exogenous L-Carnitine (Siakotos A. N., Hutchins G. D., Farlow M. R., Katz M. L., European Journal of Pediatric Neurology 5 Suppl A: 151-6, 2001) and those of the parents of the child who was afflicted with LINCL (discussed below). The child was given exogenous L-carnitine for over three years without significant metabolic changes or marked outward observations of her condition. It was only the delivery of exogenous TML to the afflicted LINCL child that yielded significant metabolic and outward, observable changes to her condition.

A discussion of the experimental results presented in the parent application showed effectiveness of TML therapy in the amelioration of several symptoms including: hyperammonemia, glutamine levels, insomnia, "nervousness" or myoclonus.

L-Carnitine may be essential or "conditionally" essential for several groups of people including: normal infants, premature infants, and both children and adults suffering from a variety of genetic, infectious, and injury-related illnesses. For example, some cardiomyopathies which afflict children are resulting from carnitine deficiency, hypoglycemia, hypoketotic, encephalopathy, Reye-like syndrome, for recurrent seizures and developmental delay, AIDS or AIDS-like conditions, over-accumulation of lipids causing myopathy, myoglobinuria, neuropathy, cardiomyopathy, ammonia overproduction, hyperammonemic syndromes, over accumulation of triacylglycrols, Batten diseases, infantile neuronal lipofuscinoses diseases (Santavvori diseases), Late infantile neuronal lipofuscinoses diseases (Jansky-Bielscowsky), Speilmeyer disease, Sjorgsen disease, Kuf diseases, Parry diseases, Juvenile or adult neuronal lipofuscinoses diseases ("NCL") disease, lysosomal accumulation of mitochondrial ATP synthase subunit and associated byproducts, ataxia and seizures, various stages of mental impairment, (e.g., learning disability, clumsiness, stumbling, impaired motor skills, and dementia, hyperandrogenism caused by NCL, defective dopamine receptors caused by NCL, epileptic fits, myoclonic epilepsy, Parkinson's disease, and Alzheimer's disease.

The experimental results presented to prosecute the parent application showed that the progress observed by the medical care-givers to the LINCL child-patient correlated with the administration of high purity TML. See Table B below.

TABLE B

Results After TML Therapy.

| Test Name | Nov. 19, 2003 | Clinical Range | Jan. 29, 2004 | Clinical Range |
| --- | --- | --- | --- | --- |
| Hgb | 14.4 | high | 14 | normal |
| HCT | 42 | high | 40.3 | normal |
| RDW | 11.5 | high | 12.3 | normal |
| ABS Lymphocytes | 2.2 | low | 2.5 | normal |
| Glycine | 50 | high | 25 | normal |
| Taurine | 24 | high | 19 | normal |
| Carnitine, Total | 40 | normal | 43 | normal |
| Carnitine, Esthers | 7 | normal | 10 | normal |
| Alanine | 87 | high | 47 | normal |
| Carbon Dioxide | 32 | high | 22 | normal |
| BUN | 2 | low | 5 | (low) (6 is norm!) |
| AST | 60 | high | 50 (high) | (40 is norm) |
| Platelets | 586 | high | 461 (high) | (369 norm) |
| Glutamine | 99 | high | 70 | normal |

Notes to the Table B:
(a) HCB = hemoglobin, HCT = Hematocrit, RDW Red Cell Distribution Width, ABS absolute, BUN Blood Urea Nitrogen, AST = Aspartate Amonotransferase)
(b) The examining physicians comments of Nov. 19, 2003 regarding Table B: (I) Alanine is elevated, this may be seen in states with increased pyruvate, (ii) Glutamine is increased, this may be seen, with Hyperammonemia.; Clinical correlation is indicated.
(c) The examining physicians comments on Jan. 29, 2004 that no significant elevation of serum amino acid was seen.
(d) The patient's glucose and potassium increased (Glucose 93 baseline to 132; Potassium 4.4 baseline to 4.8). Even though the follow up blood work was done after an all night fast, we did give her some "Gatorade" to drink before the blood test. This was given with her Klonopin to wash it down and certainly could be a contributing factor to the rise in glucose and potassium.

due to metabolic errors or deficiencies. There is data that supports treatment of some myocardial dysfunctions with L-carnitine supplementation. (Winter, S., Joe, K., Prochazka J., Francis, P., Hamilton, W., Linn, L., Helton, E. (1995) J. Child Neurol. 10, Supple 2: S45-51.)

For these and other reasons, all of which were described in detail in the parent application, it is believed that TML, or its derivatives which had been proposed in the parent application, may be used for the treatment of a human being diagnosed with one or more of the following: defects in carnitine biosynthesis pathway, inefficiency of endogeneous processes involving TML, over-accumulation of TML bound protein at the cellular level, renal failure conditions, hyperammonemic encephalopathy, over-accumulation of glutamine in the brain, reduced and deficient fatty acid metabolism and shuttling of fatty acid in to mitochondria, insufficient ATP production or subsequent energy production and all the cellular activities associated with these events, defective fatty acid oxidation It was also found during the administration of TML to the child that it was essential that high purity, therapeutic-grade TML be used for treatment purposes.

Therefore, methods of purifying the TML based compounds were invented by the team of current inventors. These inventions are listed below in the present application.

SUMMARY OF THE INVENTION

The present invention provides methods of synthesis of N-6-trimethyl-L-lysine (TML) and TML derivative compounds.

The present invention also provides a method of purifying TML and TML derivative compounds to at least 98% purity.

In the parent application Ser. No. 11/105,165, allowed on Nov. 17, 2010 to issue as a patent, it was shown by carefully compiled experimental results and other scientific demonstration, that therapeutic use of TML may successfully arrest, and in certain respects, reverse the degeneration associated with the group of progressive neurological diseases called neuronal ceroid lipofuscinoses (NCL).

The modified TML derivatives described should have similar or near-similar results and improved biochemical properties. One of ordinary skill in the art would recognize that structural derivatives of TML, such as those mentioned in this application, may participate in the same biological processes and have the same and improved biochemical properties.

Formulations or encapsulations of the compounds shown in Formulas I-VI may be used for efficient intracellular delivery and as a prodrug of TML to proceed to make endogeneous L-carnitine, and to participate in various metabolic activities in the intermediate steps of L-carnitine biosynthesis pathway. These may be used for better adsorption of modified TML into various tissues such as kidney, liver and brain. The R', R", and aminoacyl groups are expected to hydrolyze inside the cellular media with one or more intracellular esterases to release free TML. Intracellular esterases are known to hydrolyze esters (Ghosh, M. and Mitra, A. K., Effects of 5'-Ester Modification on the Physicochemical Properties and Plasma Protein Binding of 5-Iodo-2'-Deoxyuridine. Pharm. Res., 8, 771-775, 1991).

It is believed these can be used to treat a human being diagnosed with one or more of the following: defects in carnitine biosynthesis pathway, efficiency of endogeneous TML, over-accumulation of TML bound protein at the cellular level, reduced and deficient fatty acid metabolism and shuttling of fatty acid in to mitochondria, insufficient ATP production or subsequent energy production and all the cellular activities associated with this events, defective fatty acid oxidation resulting from carnitine deficiency, hypoglycemia, hypoketotic, over accumulation of triacylglycrols, lysosomal accumulation of mitochondrial ATP synthase subunit and their by-products. This is described in detail in the allowed parent patent application Ser. No. 11/105,165.

In one embodiment, the invention provides a method of synthesizing a compound represented by Formula II:

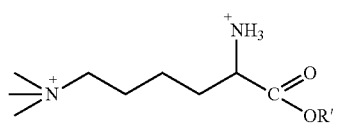

Formula II wherein R' is selected from the group consisting of an alkyl having between 1 and 5 carbon atoms and an aromatic ring.

In another embodiment, the invention provides a method of synthesizing a compound represented by Formula III:

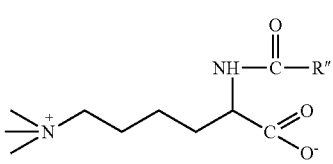

Formula III wherein R" is an alkyl having 1 to 5 carbon atoms or CH3.

In another embodiment, the invention provides a method of synthesizing a compound represented by Formula IV:

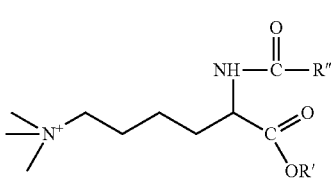

Formula IV wherein R" is an alkyl having between 1 and 5 carbon atoms, or CH3 and R' is an alkyl having between 1 and 5 carbon atoms or an aromatic ring.

In another embodiment, the invention provides a method of synthesizing a compound represented by Formula V:

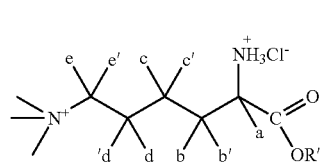

(Formula V)

wherein R' is an alkyl having 1-5 carbon atoms or an aromatic ring.

In another embodiment, the invention provides a method of synthesizing a compound represented by Formula VI:

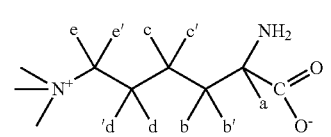

Formula VI wherein the a, b, b', c, c', d, d', e, and e' are independently selected from H, deuterium, and an alkyl having from 1 to 5 carbon atoms, and each N is independently selected from nitrogen and N15 labeled nitrogen.

In further embodiments the invention provides methods of purifying these compounds. In one such embodiment, the invention provides a method of purifying the TML compound represented by Formula I

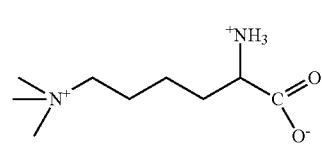

Formula I to at least 98% purity.

In another embodiment, the invention provides a method of purifying the TML derivate compounds represented by Formulas II, III, IV, V, and VI above to at least 98% purity.

The method of purifying the TML and TML-derivative compounds involves including the following steps in the process:
1. running the TML compound or derivative through an ion exchange resin column;
2. washing the ion exchange resin column with at least 4 times the volume of water as the amount of present TML compound or derivative;

3. eluting the washed TML compound or derivative from the ion exchange resin column to obtain eluted TML or derivative; and 4. triturating the eluted TML or derivative.

In a preferred embodiment, the method further involves:

5. dissolving the triturated TML or derivative into a polar solvent;

6. filtering the dissolved TML or derivative through a microglass membrane filter; and 7. lyophilizing the filtered TML or derivative at room temperature.

Although the process was outlined in the original application and is outlined in preceding paragraphs, the general process is described in detail in the Detailed Description.

The method of synthesis, which is the subject matter of this divisional application, is an improvement of the method reported in the literature and referenced in the parent application, by Frederic M. Vaz, Bela Melegh, Judith Bene, Dean Cuebas, Douglas A. Gage, Albert Bootsma, Peter Vreken, Albert H. van Gennip, Loran L. Bieber and Arnold J. A. Wanders; Clin. Chem: 48:6, 826-834, 2002).

The most critical part of this improvement is the removal of impurities and careful monitoring of the fractions during ion-exchange column purification. After the synthesis of TML from lysine, a careful collection of fractions was carried out and each fraction was monitored by thin layer chromatography, as reported in the parent application. The elution was done initially with deionized Millipore water, followed by 0.5 M aqueous (aq.) ammonia ($NH_3$), followed by 1 M aq. ammonia. The fractions were visualized by ninhydrin test on the thin layer chromatography (TLC) plate. The early and late eluting fractions were found to be of impure or undesired impurity. The purest fractions thus observed were then combined to yield TML of high purity with no visible impurities by TLC (greater than 98%), and conformed to correct mass spectral data and high-resolution proton NMR analysis.

Diagrammatic Representation of Typical Example of Synthesis of Modified TML

The proposed modifications of the aliphatic backbone have been described in ample detail in the parent application as filed. Similarly, carboxylic acid esters, amides of both the alpha amino group and the terminal amino group have been proposed in detail. An illustration of the synthesis of all deuterium backbones are shown diagrammatically from Formula IX, with the precursor all deuterated lysine, Formula VIII, using the reaction conditions of dimethyl sulfate, alkaline copper carbonate basic and highly purified distilled water to synthesize compound represented by Formula IX, followed by purification as detailed in our application. Fully deuterated lysine can be synthesized using methods reported in the literature and many deuterated lysines have been available commercially.

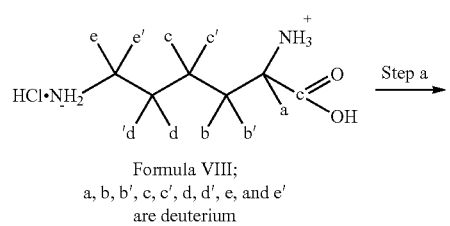

Formula VIII;
a, b, b', c, c', d, d', e, and e'
are deuterium

Step a

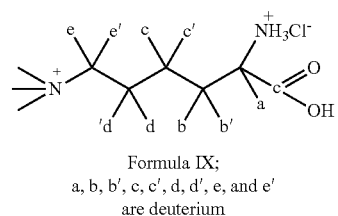

Formula IX;
a, b, b', c, c', d, d', e, and e'
are deuterium

DETAILED DESCRIPTION OF THE INVENTION

As used herein, the term "derivative" means any of Formulas II-VI. The invention incorporates both TML and TML derivatives. As such, any mention of TML also encapsulates the TML derivative compounds.

The symbol "—" represents a covalent bond.

Reference to a chain, such as an alkyl, can mean either the branched or unbranched chain unless otherwise noted.

An "alkyl", as used herein, means either a branched or unbranched alkyl chain, and includes, for example, methyl, ethyl, n-propyl, isopropyl, n-butyl, sec-butyl, isobutyl, tert-butyl, n-pentyl.

As used herein, "dilute" means ten percent or less in solution.

As used herein "excess" means a stoichiometry greater than 1:1.

A "mild base," as used herein, means a dilute base.

The phrase "pharmaceutically acceptable" indicates that the designated carrier, vehicle, diluent, excipient(s), and/or salt must be chemically and/or physically compatible with the other ingredients comprising the Formulation, and physiologically compatible with the recipient thereof.

Prophetic Example of Synthesis of TML—Carboxylic Acid Esters

As shown in equation 1, the conversion of carboxylic group of the TML carboxylic group will be achieved by acid catalyzed nucleophilic addition of methanol, ethanol and higher alcohol homologues to produce methyl ester (R'; CH3), ethylester (R'; C2H5), and higher ester respectively.

The TML methyl ester (III; R'; CH3) can be prepared by taking a suspension of TML in excess methanol, followed by saturation of the reaction mixture with anhydrous hydrogen chloride, The mixture is to be evaporated and the excess of HCL to be removed, to give crude solid. The mixture can then be neutralized carefully to neutral pH. In the absence of free carboxylic acid the quarternary ammonium nitrogen of TML methyl ester would form a hydroxide salt, The crude product can subsequently be purified by ion exchange chromatography to get pure TML methyl ester.

The higher ester homologs (III; R'; C2H5, C3H7 n and iso, C4H9, n and iso, pentyl, n and iso) can be similarly prepared under similar reaction condition. The aromatic esters can be similarly prepared. The esterification reaction generally takes longer reaction time in presence of anhydrous HCI (Equation 1).

The reaction can be shown as follows, with R' as defined above.

Equation 1

Esterification of TML

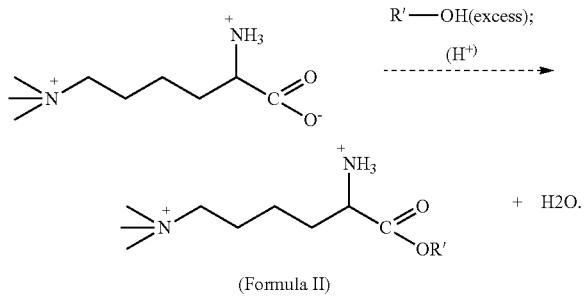

(Formula II)

Prophetic Example Synthesis of TML—Carboxylic Acid Esters and Amides

As shown in Equation 2, below, the synthesis of amidites of TML-carboxylic acid esters can be achieved in a straightforward manner from the Formula III, below, under mild basic conditions using dilute NaOH, dilute KOH, dilute barium hydroxide, or tertiary amines such as, triethylamine, diisopropyl ethylamine, and protection of the alpha-amino group with aliphatic and aromatic acid chlorides or acid anhydride, followed by neutralization of excess base, extraction of protected TML, and ion-exchange chromatography. The trimethylammonium group of the compounds Formulas V, would exist in the salt form. The acid chloride could be chosen from a group of R" protecting groups, represented by R", such as acetyl chloride, ethyl acetyl chloride, propyl acetyl (normal and iso) chloride; butyl acetyl (normal and branched) chloride; pentyl acetyl (normal and branched) chloride or the corresponding acid anhydrides. Further the acid chloride could be from a group, such as compounds represented by trifluoromethyl acid anhydride, trichloromethylacetic anhydride, and further various aromatic, substituted aromatic, heterocyclic substituted heterocyclic acid chloride can be taken for the substitution and protection of the alpha amino group of TML derivative represented by Formula III. The higher homologs of Formula V can similarly be prepared.

(Equation 2)

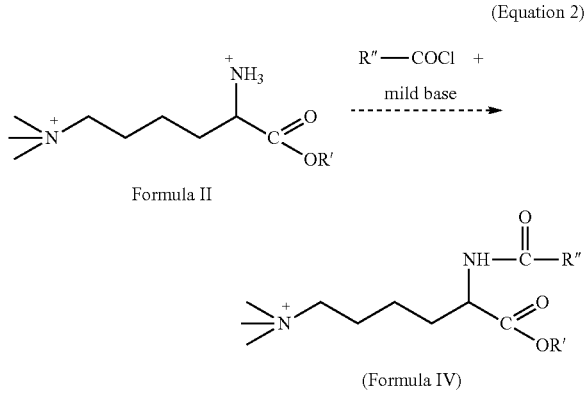

(Formula IV)

Prophetic Example of Synthesis of TML—Amides (Formula III)

As shown in equation 3, below, the synthesis of amidites of TML-carboxylic acid (Formula IV) can be similarly achieved best from TML under basic conditions using dilute NaOH, dilute KOH, dilute barium hydroxide, or tertiary amines such as, triethylamine, diisopropyl ethylamine, and aliphatic and aromatic acid chlorides or acid anhydride, followed by treatment of the reaction mixture with water to hydrolyze the mixed anhydride formed on the carboxylic function. This step was followed by extraction of protected TML, and ion-exchange chromatography. The trimethylammonium group of the compound of Formula IV, would preferably exist in the internal salt form. R" is an alkyl having 1 to 5 carbon atoms or CH3. In another embodiment, the acid chloride is trifluoromethyl acid anhydride and trichloromethylacetic anhydride. The skilled artisan will understand that the same or similar reaction can be carried out with R" being an aromatic ring, a substituted aromatic ring, a heterocyclic ring, and a substituted heterocyclic ring, the acid chloride of these can thus protect the alpha amino group of TML derivative represented by Formula III. The higher homologs of Formula V can similarly be prepared.

(Equation 3)

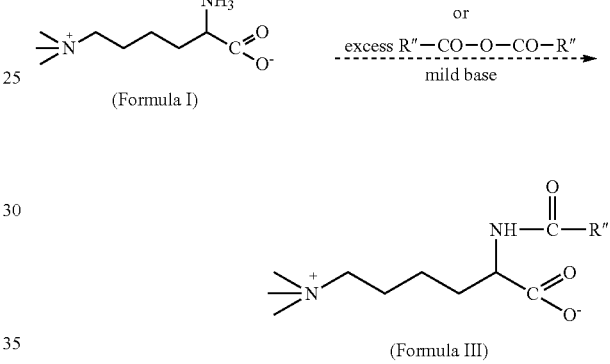

Prophetic Example of Synthesis of Aliphatic Chain Substituted TML (Formula VI)

As depicted in equation 4, below, the synthesis of aliphatic chain substituted TML can best be obtained starting with aliphatic chain substituted L-lysine. Many such derivatives of Lysine are available. Thus as an example, tetradeutrated L-lysine (L-lysine 4,4,5,5-D4 L-lysine 0.2HCl).

Compounds within Formula (VII) are commercially available from Cambridge Isotope Laboratories Inc., Andover, Mass. Additional deutrated L-Lysine can similarly be obtained commercially or custom produced by such companies. From such aliphatic chain modified L-Lysine, aliphatic chain modified TML can be produced by the method outlined in the method of synthesis of TML in the present invention. Since the aliphatic chain substitutions proposed in claim are chemically non reactive, the L-Lysine to TML conversion would follow straightforward similar to our example of TML synthesis. The value of a, b, b', c, c', d, d', e, e' can independently be selected from the group consisting of H, deuterium, methyl, ethyl, propyl (normal and iso), butyl (normal and branched), and pentyl (normal and branched). Subsequently the carboxylic group could be esterified as exemplified in equation 1, above, leading to synthesis of compounds with R' being H, deuterium in one or more carbons of the aliphatic chain of TML, methyl; ethyl; propyl normal and iso); butyl (normal and branched); pentyl (normal and branched), Further, R' could be aromatic, substituted aromatic, heterocyclic, substituted heterocyclic, can be synthesized similarly.

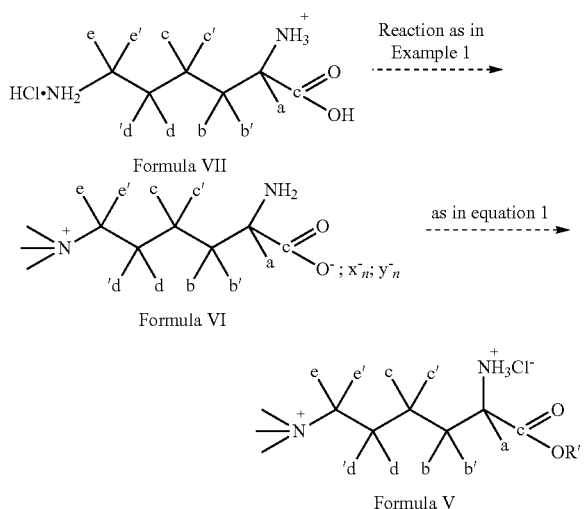

Synthesis of 1-Lysine, having carbon bound deuterium and N15 labelled L-lysine can be achieved using the procedure as demonstrated by Weissman and Schoenheimer (N. Weissman R. Schoenheimer, J. Biol. Chem. 140,549, 1943~. The procedure, which consists of a multistep process, allows deuterium and N15 labeling in the process. With appropriately labeled lysine, the synthesis of appropriately labeled TML will proceed as demonstrated in Equation 1, outline in the improved process of making TML.

The selective synthesis of esters of TML, and other derivatives, as shown in the above examples can be achieved based on the principle and practical details abundant in literature for selective esterification of the carboxylic acid functionality of large number of amino acids. The details can be found in a number of text books of amino acid chemistry, such as (i) Amino Acid Derivatives, A Practical Approach, Editor Graham C. Barrett, Oxford University Press, 1999 (ii) Amino Acids and Peptide Synthesis by John Jones, Oxford University Press, 1992.

Improved Method of Synthesis and Purification of TML and TML Derivatives

Starting Raw Material: L-lysine HCl (Sigma-Aldrich, St. Louis, Mo.), dimethylsulfate (99.99%) Sigma-Aldrich, St. Louis, Mo.), alkaline copper carbonate (Sigma-Aldrich, St. Louis, Mo.), double distilled water (highly purified), Whatman 3MM Chromatography blotting paper (Whatman Inc., Florham Park, N.J.), sodium hydroxide (NaOH, 99%+) (Sigma-Aldrich, St. Louis, Mo.), Dowex SOWX8 ion exchange column (The Dow Chemical Company, Midland, Mich.).

L-lysine HCL (50 gm; 0.274 mol) was dissolved in distilled water (500 mL) and copper carbonate basic (72 gm; 0.326 mol) was added. The mixture was boiled at 85 centigrade for 10 minutes.

The reaction mixture was cooled to room temperature and filtered with Whatman 3MM paper. The clear filtrate was mixed with dimethylsulfate, 100 mL (1.055 mol) at room temperature, after which 325 mL of aq. sodiumhydroxide solution (10% aq.; 1.055 mol; w/v, in dd water) was added drop-wise during 30 minutes, then stirred at room temperature for 60 min.

A 17" height×2" dia Dowex5OW×8 ion exchange column ($H^+$ form) was washed with deionized water prior to the addition of the TML solution.

The solution containing the TML was then added to the Dowex5OW×8 column.

The column was copiously washed with 500 mL of distilled water. This process was repeated with 1700 mL water and 1000 mL and 700 mL fractions were collected. The collection and monitoring of these fractions were accomplished by thing layer chromatography (TLC) and ninhydrin color tests.

Subsequently, 2M ammonium hydroxide solution was run and 8 fractions (each fraction 50 mL, followed by 100 mL) were collected. TLC analysis was performed on all the fractions (tic system: MeOH:water:Aceticacid::80:10:10). These fractions are detailed in Table C below.

TABLE C

Tabular Summary of Ion-Exchange Column Purification Steps.

| Fraction# | Solvent | Volume | Result |
|---|---|---|---|
| 1 | $H_2O$ | 50 | Negative |
| 2 | 0.5M aq $NH_3$ | 75 | Negative |
| 3 | 0.5M aq $NH_3$ | 75 | Negative |
| 4 | 0.5M aq $NH_3$ | 50 | Negative |
| 5 | 1M aq $NH_3$ | 50 | Positive |
| 6 | 1M aq $NH_3$ | 50 | Positive |
| 7 | 1M aq $NH_3$ | 50 | Positive |
| 8 | 1M aq $NH_3$ | 50 | Positive |
| 9 | 2M aq $NH_3$ | 50 | Positive |
| 10 | 2M aq $NH_3$ | 100 | Positive |
| 11 | 2M aq $NH_3$ | 100 | Positive |
| 12 | 2M aq $NH_3$ | 100 | Positive |
| 13 | 2M aq $NH_3$ | 100 | Negative |

Table C Notes:
1. The Ion- Exchange purification on Dowex 50WX8 inch column length 17 "heightX2" diameter. First elution (Fraction 1) 100 ml water; subsequent elution in .5M aq $NH_3$ 200 ml; subsequent elution in 1M aq $NH_3$, 200 ml; followed by last elution in 2M aq $NH_3$, 500 ml.
2. TLC solvent system methanol:water:acetic acid:: 80:10:10 was used to check all fractions after staining the TLC plate with ninhydrin solution and observing colored stained band.
3. Fractions 5 to 10 were pure fractions, so they were combined and evaporated.

The eight fractions were combined and evaporated to yield an oil. The oil was subsequently lyophilized at room temperature to yield a solid.

The solid was triturated in acetonitrile and filtered and washed with acetonitrile again.

The solid was dissolved in methanol/water (95:5::Methanol:ddWater) and filtered with glass micro filter paper and the filtrate was evaporated and lyophilized.

Large-Scale Purification of TML

A larger scale synthesis has been achieved, which is further amenable to large-scale production of TML. The larger scale synthesis of TML incorporating step of final clean up to achieve purity of at least 98% or greater, and free of foreign materials, has been demonstrated. The procedure in prior art literature does not teach synthesis of high purity TML or TML derivative, which could be applicable to pharmaceutical-grade product. Therefore, new methods were invented for the purpose.

The purification steps that allow larger scale synthesis can be described as follows:
1. Running crude TML or TML derivative through an ion exchange resin column;
2. Washing the ion exchange resin column with at least 4 times the volume of water as the amount of present crude TML or TML derivative;
3. Eluting the washed TML or TML derivative from the ion exchange resin column;
4. Freezing the eluted solution and then lyophilize at room temperature to prevent or minimize any decomposition of obtained TML or TML derivative; and 5. Triturating the lyophilized solid TML or TML derivative.

In another embodiment, the following additional steps may include:

6. Dissolving the triturated TML or TML derivative into a polar solvent;
7. Filtering the dissolved TML or TML derivative through a microglass membrane filter; and
8. Lyophilizing the filtered TML or TML derivative at room temperature.

This process is an improvement of what is disclosed in Frederic M. Vaz, Bela Melegh, Judit Bene, Dean Cuebas, Douglas A. Gage, Albert Bootsma, Peter Vreken, Albert H. Van Gennip, Loran L. Bieber And Ronald J. A. Wanders, Clin. Chem. 48:6, 826-834, 2002.

Quality Control

The following quality control parameters were obtained:

A. TLC' Samples 1 and 2 were purified TML made according to the invention. Sample 3 was a reference TML purchased from Sigma-Aldrich. The tic plates were Baker-flex silica gel 1B-F. TLC Purity' was greater than 99%, and the spots were observed after staining the spot with ninhydrin (10% in methanol) (FIG. 1).

B. 1H NMR: The 1H NMR (Proton in $D_2O$) was run on 300 MHz; 1.3932 ppm (methylene at C-2; 2H, broad singlet), 1.6643 ppm (methylene at C-3 2H, broad, multiplet); 2.13 ppm (methylene at C-4; 2H, broad singlet), 3.2928 ppm (methylene proton at C-5, 2H; triplet); 3.2167 ppm (alpha H; 1H; triplet); 3.0798 ppm (trimethyl H' s; 9H)(FIGS. 2a and 2b).

C. Mass Spectrum: Chemical Formula $C_9H_{20}N_2O_2$, Molecular weight; 189.28. Four major fragmentation peaks were observed in positive mode; m/e 189.3, m/e 211.2 (+Na ion), m/e 377.5 (possibly dimer formation) and m/e 399.5 (possibly Na+ ion addition on dimmer) (FIG. 3).

Salt Formation

The TML synthesized (as described above) had no external salt. The carboxylic group (which is negatively charged) and the trimethyl group (which is positively charged) form an internal salt. The alpha amino group picks up the proton from the ionized carboxylic group. The molecular weight of this TML is 188.3 From our Mass Spectral analysis (positive ion) we get the molecular ion peak at 189.28 (One extra mass in positive ion is proton adding from matrix). This data confirms MW of 188.3.

The skilled artisan will understand that TML can exist as an external salt as well, such as a potassium salt.

We claim:

1. A process for the purification of a compound of formula 1

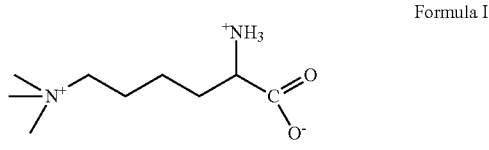

Formula I $X_n^-$; $Y_n^-$ wherein the counter ions $X^-_n$ and $Y^-_n$ are selected from the group consisting of OH, halides, sulfhydryl, carboxylic, phosphines, amines, organic anions, inorganic anions, and a mixture of organic and inorganic anions, and n is 0 or greater; wherein the process comprises the following sequence of steps:

(i) Run crude trimethyl-L-lysine (TML) through an ion exchange resin column;
(ii) Wash the ion exchange resin column with a volume of water that is at least 4 times the amount of crude TML present;
(iii) Elute the washed TML from the ion exchange resin column using several different concentrations of aqueous ammonia wherein the concentrations range from about 0.5M aqueous ammonia, about 200 mL to about 2M aqueous ammonia, about 500 mL, or using suitable concentrations of a base;
(iv) Collect said multiple fractions eluted in step (iii);
(v) Carry out analysis of each fraction collected in step (iv) for any visible impurities;
(vi) Combine the fractions from step (v) that do not exhibit any visible impurities and eliminate the fractions from step (v) that do exhibit visible impurities;
(vii) Subject said combined fractions from step (vi) to thin layer chromatograph (TLC) analysis to identify fractions comprising an approximate purity level greater than 98%;
(viii) Bring the combined fractions from step (vii) to −20° C. with outside cooling;
(ix) Lyophilize the frozen fractions at room temperature; and
(x) Triturate the obtained product with a non-polar solvent.

2. The process of claim 1 comprising the following additional steps:

(i) Dissolve the triturated product of step (x) of claim 1 into a polar solvent;
(ii) Filter the dissolved TML through a microglass membrane filter; and
(iii) Lyophilize the filtered TML at room temperature.

* * * * *